United States Patent [19]
Van Den Oever

[11] Patent Number: 5,450,982
[45] Date of Patent: Sep. 19, 1995

[54] FILTER CHANGE MECHANISM

[76] Inventor: Menno H. Van Den Oever, P.O. Box 98485, Sloane Park, 2152, South Africa

[21] Appl. No.: 197,487

[22] Filed: Feb. 16, 1994

[30] Foreign Application Priority Data

Feb. 18, 1993 [ZA] South Africa .................. 93/1122

[51] Int. Cl.6 .............................................. B65H 3/44
[52] U.S. Cl. .................................. 221/93; 221/96; 221/102; 221/239; 221/264; 221/268; 134/133
[58] Field of Search ............... 221/224, 236, 238, 239, 221/258, 263, 264, 265, 266, 267, 268, 93, 22, 66, 96, 97, 102; 134/133; 73/61.73, 61.63, 61.67; 222/189

[56] References Cited

U.S. PATENT DOCUMENTS

| | | | |
|---|---|---|---|
| 1,699,504 | 1/1929 | Lynch | 221/238 X |
| 2,385,521 | 9/1945 | Mead | 221/238 X |
| 4,389,879 | 6/1983 | Bach et al. | 73/61.73 |
| 5,082,150 | 1/1992 | Steiner et al. | 222/189 |
| 5,383,573 | 1/1995 | Balsimo | 221/264 |

*Primary Examiner*—William E. Terrell
*Assistant Examiner*—Dean A. Reichard
*Attorney, Agent, or Firm*—Popham, Haik, Schnobrich & Kaufman, Ltd.

[57] ABSTRACT

A filter change mechanism is disclosed. The mechanism includes a filter dispensing device, a device for releasably clamping a filter in a fluid line, a filter discharge device. Also included in the mechanism is a device for conveying a filter dispensed by the filter dispensing device to the fluid line for use in filtration and for conveying a used filter to the discharge device.

14 Claims, 3 Drawing Sheets

FILTER CHANGE MECHANISM

BACKGROUND TO THE INVENTION

The present invention relates to filter change mechanisms.

It is designed mainly for use in the dissolution testing of sample solutions, but has application in any industry where filters are incorporated in fluid lines where media/solutions are required to be filtered. The filters are generally required to be replaced when they become blocked or offer a high flow restriction.

It is an object of the present invention to provide a filter change mechanism for automatically replacing filters in fluid lines.

SUMMARY OF THE INVENTION

A filter change mechanism according to the invention, includes a filter dispensing device, a device for releasably clamping a filter in a fluid line, a filter discharge device and conveying means to convey a filter dispensed by the filter dispensing device to the fluid line for use in filtration and to convey the used filter to the discharge device.

While any suitable conveyor may be used, in a preferred form the conveying means includes a slide. The movement of the slide may be arcuate but in a preferred form is linear.

The dispensing device is suitably made up of a filter holder which holds a number of filtors stacked in a single or multiple tier. A preferred form of a dispensing device is a tube (into which unused filters are loaded) with an open end at the bottom.

Clamping of the filter may be accomplished in any suitable manner but is preferably pneumatically operated.

In one preferred form clamping is achieved by a pneumatic piston where the fluid line passes through the piston from the outlet of the filter. When the piston is in the "clamped" position, the filter is compressed between the piston and a base which accommodates the fluid line, connecting the inlet of the filter. Note the direction of flow in the fluid line can be reversed. The piston and base may have seals which seal against each side of the filter when in the "clamped" position, hereby completing the fluid path through the filter.

Discharging of the used filter may be accomplished in any suitable manner but is preferably discharged by an eject pin or ram which ejects the filter into the discharge device in order to clear the conveying means so the operation can be repeated.

A preferred form of a discharge device is a tube with an open end at the bottom fitted with an effective retaining ring or similar obstruction near the bottom of the tube to prevent the used filters from falling back into the locating slide aperture.

BRIEF DESCRIPTION OF THE DRAWINGS

In the accompanying drawings which illustrate by way of example a preferred embodiment of the invention.

DETAILED DESCRIPTION OF THE DRAWINGS

Figure 1:
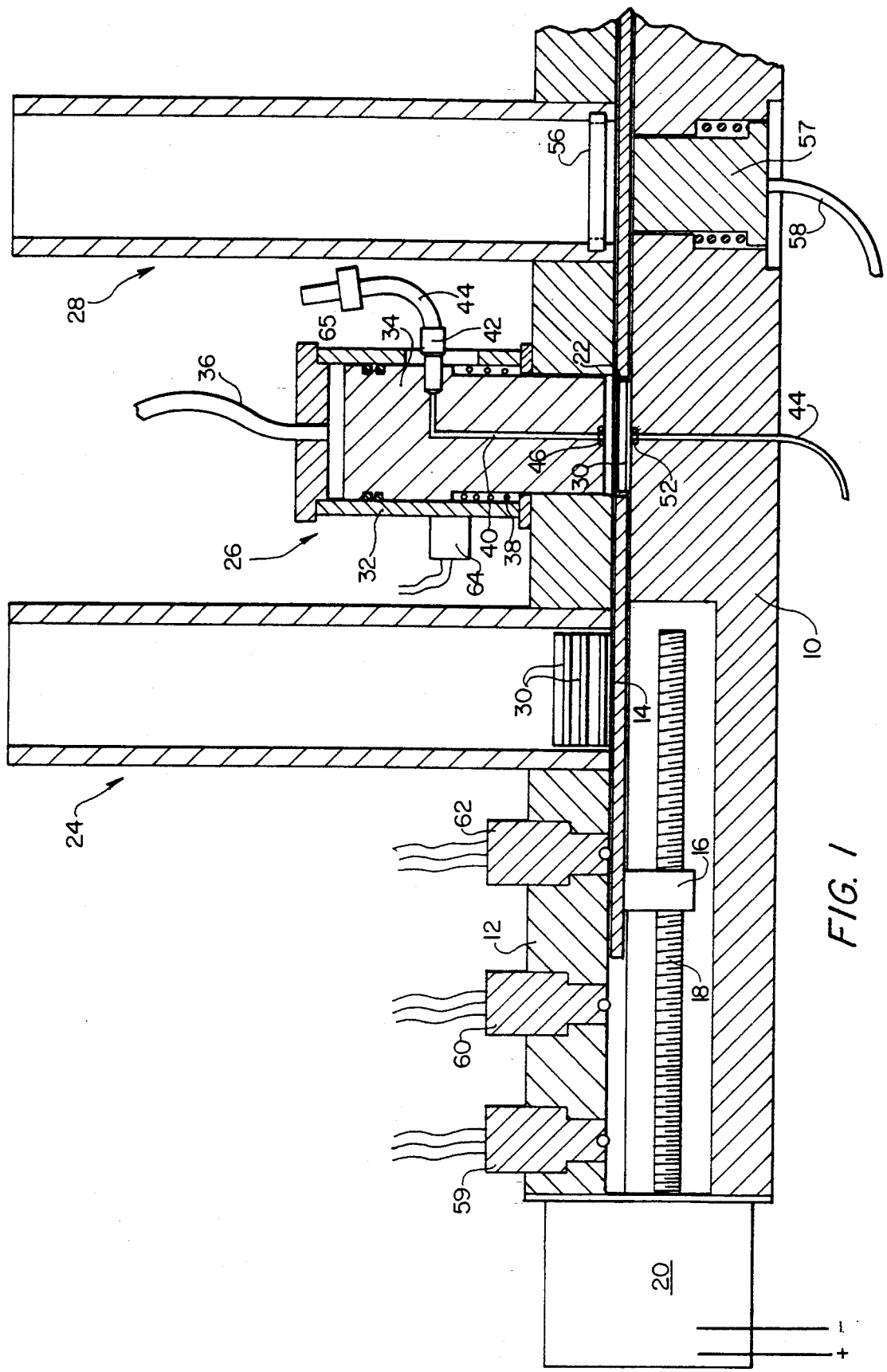
FIG. 1 is a schematic side view of a filter change mechanism according to one embodiment of the invention.

The filter change mechanism is designed to incorporate filters into fluid/sampling lines through which test solution is withdrawn from the test solution vessel. It is used for any application in which a sample or a fluid line is required to be filtered.

The filter change mechansim shown comprises a filter dispenser 24, a filter clamping device 26 and a discharge device 28 fitted to a base block 10.

The filter dispenser 24 consists of a hollow open ended cylinder into which filters 30 are loaded.

In use a stack of filters 30 is loaded into the filter dispenser 24. mechanism which rotates the locating slide so that the filter is moved from the dispensing position to the clamping position and rotated further to the discharge position.

When the filter 30 in the locating slide member 14 reaches the filter clamping device 26, the slide 14 is stopped.

The filter clamping device 26 includes a cylinder 32 containing a piston 34 which can be moved down pneumatically by air fed through the air line 36 against a piston return spring 38. With the cylinder 32 connected to the air line 36 the piston 34 moves downwardly to clamp the filter 30 against the base block 10.

In another form, piston 34 can be replaced with any mechanism which is capable of clamping the filter against a base 10, such as a solenoid operated block replacing the piston 34. The seals 46 and 52 serve to ensure a fluid tight junction against each side of the filter. The use of suitable materials for the piston 34, the base 10 and/or the filter 30 may render seals 46 and 52 unnecessary.

Fluid is then withdrawn through sampling line 44, to the filter inlet, through the filter 30, the bore 40 in the piston, the port 42 and on the sampling or filtered stage.

At one end, a locating slide 14 has a threaded bush 16 which operatively engages a screw 18 driven by an electric motor 20. The slide has an aperture 22 into which the filter loads.

At the start of a sequence, the locating slide member 14 is to the far left of the drawing in which position the filter aperture 22 will lie directly beneath the filter dispenser 24 allowing the bottom filter 30 in the stack to gravitate into the filter aperture 22. The locating slide 14 depth/thickness (i.e. the aperture depth) is similar to the filter 30 width to allow only one filter to fall under gravity into the locating slide aperture 22. In another form, the dispensing device 24 could incorporate a device (not shown) to load only one filter 30 into a locating slide aperture of any depth.

When the motor 20 is now started the locating slide member 14 will move linearly to the right conveying the filter 30 toward the filter clamping device 26. In another form the locating slide could be moved pneumatically or by means of any suitable method. In this embodiment the locating slide is of a linear form and is moved linearly to the clamping and discharge positions respectively. This invention is not restricted to a linear filter change mechanism as a rotary locating slide in the form of a circular platter can operate as effectively under the same principle of operation with the dispensing clamping and discharge positions located on an arc of a circle with a suitable driver.

At the end of the test, the air pressure line 36 vents and the piston 34 returns to its upper position under the influence of the piston return spring 38, releasing the filter 30. The motor 20 is once agian started, moving the filter 30 in the aperture 22 to the filter discharge device 28.

The filter discharge device 28 includes an open-ended bottom tube 54 having located in the base thereof, a retaining ring 56 having an internal diameter slightly less than that of the filter 30. Beneath the tube 54 in the base block 10 is a pneumatic ram 57 connected to an air pressure line 58.

The pneumatic ram 57 is then operated to push the filter out of aperture 22, to force it through the retaining ring 56, which yields to permit this, into the discharge device 28. The discharged filter 30 is prevented from falling back into the aperture 22 by the retaining ring 56 which resiles to its original condition.

The retaining ring 56 can be replaced by any retaining clip, O-ring or any suitable mechanism to prevent the filter from falling back into the locating slide aperture 22.

The pneumatic ram 57 can also be replaced by an ejector pin which ejects the used filter out of the locating slide aperture 22 to any waste chute or container. In another form the locating slide could move the filter over a chute or hole where the filter is discharged automatically under gravity to waste.

The slide member 14 is then returned to the left ready for the start of a new sequence. It should also be recorded that this invention is not limited to one set constituting one dispenser device, one clamping device and one discharge device, but can incorporate any number of these sets in any array or circular arrangement to filter a number of sample solutions simultaneously.

Figure 2:
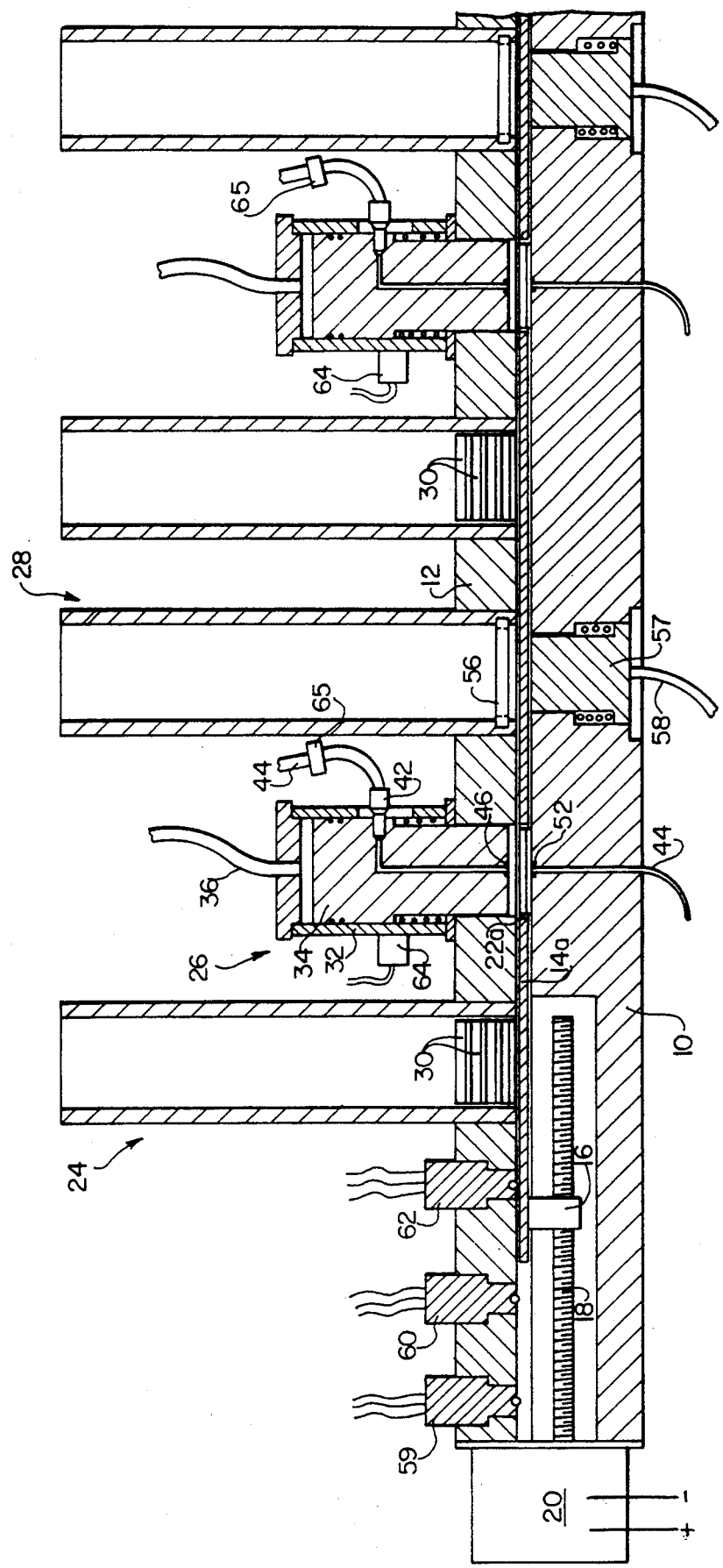
FIG. 2 shows a filter change assembly for batch dissolution testing incorporating the mechanism of FIG. 1.

One such arrangement is depicted in FIG. 2. The base block 10 has fitted to it a number of sets (two are shown) each comprising a filter dispenser 24, a clamping device 26, and discharge device 28, a common locating slide 14a similar to the slide 14 is driven by a screw drive in a similar manner to the slide 14. The slide 14a has therein spaced filter aperture 22a equal in number to the number of sets. The assembly shown permits simultaneous multiple filter change and dissolution testing to be effected.

An option which this invention utilises is that the sequential movement of the slide member is electronically controlled, and employs suitable contact switches such as those shown at 59, 60 and 62 for automatic slide position sensing, of dispensing, clamping and discharging positions.

The contact switch 64 detects when the piston 34 moves down too far indicating the absence of a filter 30 in the filter clamping device 26.

The invention thus provides a fully automated filter changer when the pressure sensing device 65 initiates the controlling device which then automatically changes the filter 30 or when required.

Figure 3:
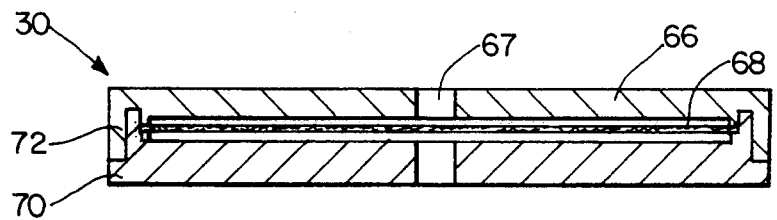
FIG. 3 shows a filter suitable for use in a filter change mechanism of the invention.
Figure 4:
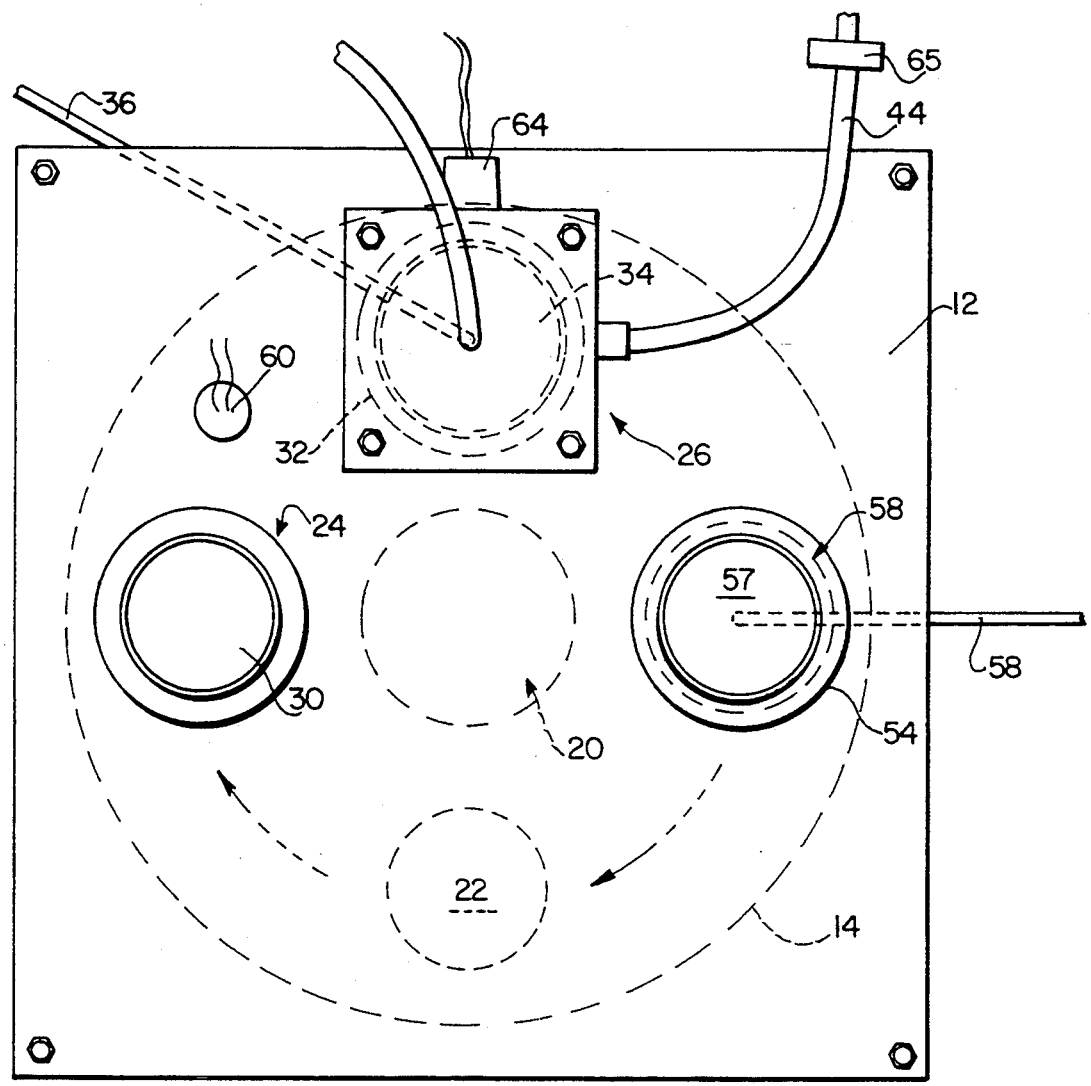
FIG. 4 shows a filter change mechanism according to another embodiment of the invention in which the movement of the slide is arcuate.

Referring to FIG. 3 there is shown a filter 30 which is suitable for use with the filter change mechanism of the invention. It consists of two identical half shells 66 with a filter membrane 68 sandwiched between the two shells 66. Each shell 66 has in it a central orifice leading to the membrane 68. The lower shell 66 has a radial flange 70 on which the skirt 72 of the upper shell seats. It is to be noted that since the filter is totally symmetrical about the plane of the filter membrane 68, no orientation of the filter 30 is required when loading the filter 30 into the filter dispenser 24 in order to ensure that the filter is properly disposed for the dissolution testing procedure.

The present invention is not limited to the precise constructional details described and many variations in detail are possible without departing from the spirit and scope of the invention.

I claim:

1. A filter change mechanism including a filter dispensing device, a device for releasably clamping a filter in a fluid line, a filter discharge device and conveying means to convey a filter dispensed by the filter dispensing device to the fluid line for use in filtration and to convey a used filter to the discharge device.

2. A filter change mechanism as claimed in claim 1 in which the conveying means includes a slide.

3. A filter change assembly as claimed in claim 1 in which the conveying means consists of a slide having a plurality of filter locating apertures therein.

4. A filter change mechanism as claimed in claim 2 in which the movement of the slide is arcuate.

5. A filter change mechanism as claimed in claim 2 in which the movement of the slide is linear.

6. A filter change mechanism as claimed in claim 1 in which the dispensing device includes a vertically disposed filter holder adapted to hold a number of filters in a stack.

7. A filter change mechanism as claimed in claim 6 in which the filter holder is in the form of a tube which is open at the bottom.

8. A filter change mechanism as claimed in claim 1 in which the clamping device includes a pneumatic piston in the fluid line having a passage therethrough which communicates at one end with the fluid line and at the other end with the outlet of the filter.

9. A filter change mechanism as claimed in claim 8 in which the clamping means further includes a base which accommodates the fluid line and which connects to the inlet of the filter, the filter being releasably clamped between the piston and the base.

10. A filter change mechanism as claimed in claim 1 in which the discharge device includes an eject member adapted to eject the used filter into the discharge device in order to clear the conveying means.

11. A filter change mechanism as claimed in claim 10 in which the discharge device includes a tube which is open at the bottom and having therein retaining means adapted to retain the ejected filter in the tube.

12. A filter change mechanism including a base to which is fitted at spaced intervals a filter dispensing device, a device for releasably clamping a filter in a fluid line and a filter discharge device and a slide having an aperture therein to accommodate a filter, the slide being movable over the base to convey the filter from the filter dispensing device to the filter clamping device and thence to the filter discharge device.

13. A filter change assembly including a plurality of sets each comprising a filter dispensing device, a filter clamping device and a filter discharge device and means for simultaneously conveying a plurality of filters between members of the sets, said members comprising said filter dispensing device, said filter clamping device, and said filter discharge device.

14. A filter change assembly as claimed in claim 13 including a base, a plurality of said sets fitted to the base, a slide having therein spaced filter locating apertures equal in number to the number of sets, and means to move the slide over the base to convey the filters simultaneously between the members of the sets.

* * * * *